United States Patent
Connor

(10) Patent No.: US 7,204,815 B2
(45) Date of Patent: Apr. 17, 2007

(54) MASTOID EAR CUFF AND SYSTEM

(75) Inventor: Georgia K. Connor, 29020 Agoura Rd. A-8, Agoura Hills, CA (US) 91301

(73) Assignee: Georgia K. Connor, Agoura, CA (US)

( * ) Notice: Subject to any disclaimer, the term of this patent is extended or adjusted under 35 U.S.C. 154(b) by 189 days.

(21) Appl. No.: 10/915,788

(22) Filed: Aug. 11, 2004

(65) Prior Publication Data
US 2006/0036200 A1 Feb. 16, 2006

(51) Int. Cl.
*A61H 1/00* (2006.01)
(52) U.S. Cl. .............. 601/46; 601/47; 601/76
(58) Field of Classification Search ........ 128/864–868; 601/46, 47, 76
See application file for complete search history.

(56) References Cited

U.S. PATENT DOCUMENTS 3,795,014 A * 3/1974 Simpson et al. .............. 2/209
6,229,901 B1 * 5/2001 Mickelson et al. ......... 381/371
2004/0037428 A1 * 2/2004 Keller ........................ 381/60
2005/0096561 A1 * 5/2005 Conn et al. ................. 600/559

OTHER PUBLICATIONS

Peniston, Eugene G., et al.; "Alcoholic personality and alpha-theta brainwave training," Medical Psychotherapy, 3:37-55, 1990.
Robbins, Jim; "Excerpt: Wired For Miracles?"; Psychology Today, Jun. 1998.
O'Brien, Joan; "EEG biofeedback gaining admirers", Salt Lake Tribune, Sep. 8, 1998, pp. 1-4.
"Stress Management By Biofeedback", Spinoff 1997.
von Hilsheimer, George, Ph.D., "Biofeedback within 45 minutes of Disney World", Spokane.net.
KSL-TV Special Series: "Mind Games", Information from a Special Report on the Channel 5 Eyewitness News at 10.
Alphasonic Soundwave Therapy Brochure XCELR8R II Personal Relaxer Owner's Manual, Mind Gear Inc. 1995.

* cited by examiner

*Primary Examiner*—Michael A. Brown
(74) *Attorney, Agent, or Firm*—Fulwider Patton LLP

(57) ABSTRACT

A system for treating brain function including a signal generator and an ear cuff. Various modalities of treatment are possible including approaches for enhancing learning, and stimulating alertness and clearing emotions.

20 Claims, 3 Drawing Sheets

MASTOID EAR CUFF AND SYSTEM

BACKGROUND OF THE INVENTION

The present invention relates to the treatment of brain function and more particularly, to approaches for accelerated learning and treating behavior problems as well as devices to accomplish the same.

It has been estimated that as much as ten percent of all children enrolling in the first grade in the United States demonstrate signs of learning disorders. In the year 2000, more than twenty million school children have been recommended or prescribed pharmaceuticals by schools and physicians as an answer to students with Attention Deficit Disorder (ADD) or Attention Deficit with Hyperactivity Disorder (ADHD). People suffering from ADD or ADHD are faced with years of taking medications during formative years until they reach maturity. These individuals are generally not equipped to progress through advanced education or are unable to get or keep jobs. Additionally, such individuals often have an inability to meet with demands of other people's schedules and timetables or face simple environmental factors such as fluorescent lights in public buildings which can prohibit them from working productively for long periods of time. Such individuals also can suffer from sleep disorders which contribute to their general inability to be punctual while also contributing to weakening their immune systems, such symptoms being exhibited in lost days from work. Financial stress, emotional stress and the lack of self-esteem exacerbate the common tendency of these people to turn to coping mechanisms in the form of substance abuse or alcoholism.

Interestingly, neurofeedback research has identified a common thread in the EEG brainwaves of alcoholics. That is to say that individuals who abuse the use of alcohol demonstrate unusually low production of alpha waves even when their eyes are closed, as compared to the population that chooses not to consume alcohol. Of course, certain EEG Alpha/Theta protocols are designed specifically to remedy such a condition.

It is now a commonly held belief in the medical community treating patients with ADD and ADHD that such individuals for the most part have underactive central nervous systems. Therefore, it is not surprising to see individuals so inflicted self-medicating with excedrine, speed or cocaine as an answer to increase functional performance levels in attention span. While it may make these individuals feel like they can get things done within the timeframe of other individuals, the experience is short lived and the price has dangerous and costly consequences.

A number of other disorders affect both learning and one's effectiveness in today's society. Such disorders include dyslexia, dysgraphia, phonological processing problems, depression, anxiety, insomnia, brain trauma, as well as other learning disabilities substance abuse and behavioral problems. These conditions can effect an individual in minor ways or it can be so severe as to effectively incapacitate the effected person.

What is needed and heretofore unavailable is an approach to treat a broad range of learning and behavior challenges which confront more than twenty million Americans. An acceptable approach would be one where the treated individual can be placed back into the mainstream as quickly as possible and to avoid the need for ongoing, limitless reinforcement or conventional treatment modalities.

The present invention addresses these and other needs.

SUMMARY OF THE INVENTION

Briefly and in general terms, the present invention is directed toward a system for facilitating the treatment of brain function. In one aspect, a treated individual is taken to higher levels of functionality and effectiveness. The patient is provided with the ability to achieve deeper states of relaxation and more profound states of attention, which in turn, results in greater ability to focus and concentrate as well as to acquire higher states of awareness.

In one embodiment, the present invention is embodied in a portable, lightweight auditory device. A microprocessing chip contained in the auditory device is capable of producing multiple frequencies of brainwaves in a patient. An auditory sub-assembly is also provided as is a power assembly. The circuitry is also provided to accomplish the alteration of the frequencies being employed.

In one particular embodiment, the auditory sub-assembly includes at least one auditory lead outlet in communication with a dual channel lead. An auditory lead can be configured to be hooked over each ear in the form of a cuff assembly. The cuff assembly includes a hooking portion or ledge and a mastoid process engaging member. The assembly also includes a power supply via battery and adapter as well as circuitry controlling frequency generation.

In other aspects, the present invention is adapted to treat symptoms associated with various conditions. Energy can be generated at frequencies to improve cocentration, induce relaxation, increase alertness or facilitate learning.

Other features and advantages of the present invention will become apparent from the following detailed description, taken in conjunction with the accompanying drawings, which illustrate, by way of example, the principles of the invention.

DETAILED DESCRIPTION OF THE INVENTION

Figure 1:
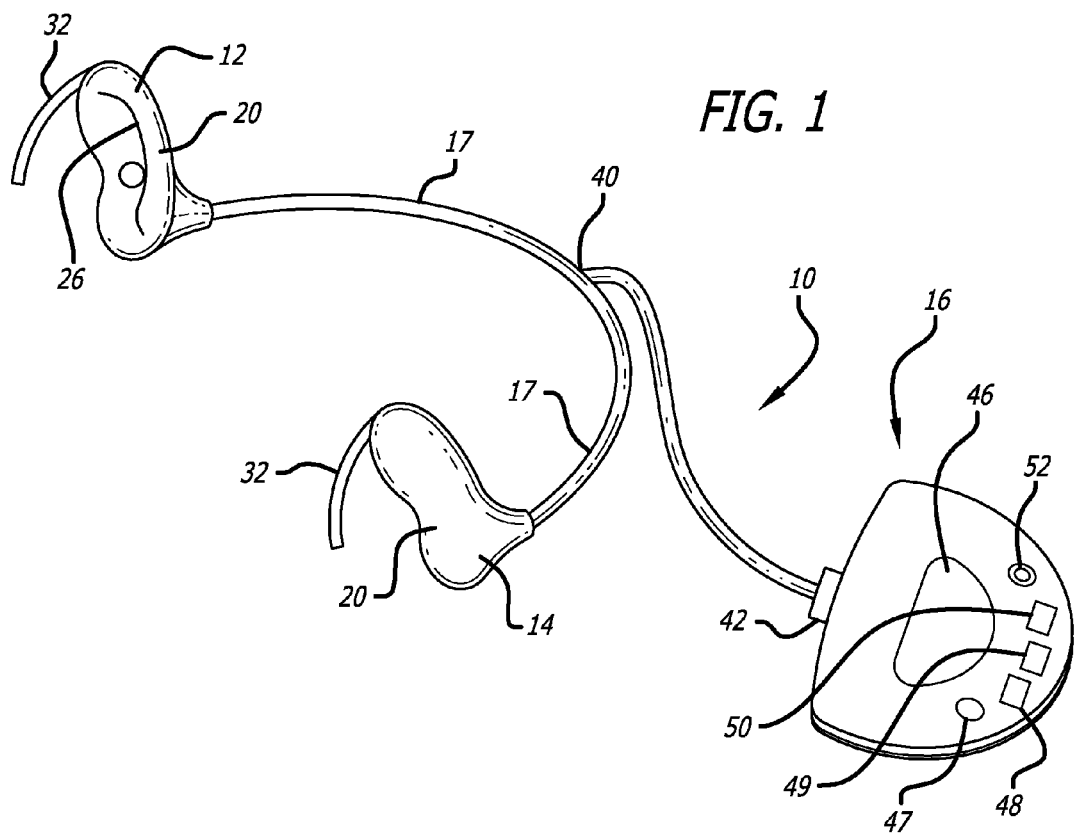
FIG. 1 is a perspective view, depicting a brain treatment system of the present invention.

Referring now to the drawings, which are provided for example and not by way of limitation, the present invention is directed to a system for treating brain function. It has been found that a correlation exists between certain states of consciousness and specific EEG frequencies. Accordingly, the present system involves programs based on brainwave frequencies and their respective harmonics.

More specifically, the present invention is designed to stimulate synchronization of the right and left hemispheres of the brain. Once the hemispheres to the brain are in-sync, various benefits are accorded to the patient. Benefits include improved learning as well as the ability to relax, re-focus, re-center, re-energize, and heightened short-term memory, enhance creative expression, improve spelling, improve problem solving, relieve performance anxiety and aid in mental preparation for any activity.

Figure 2:
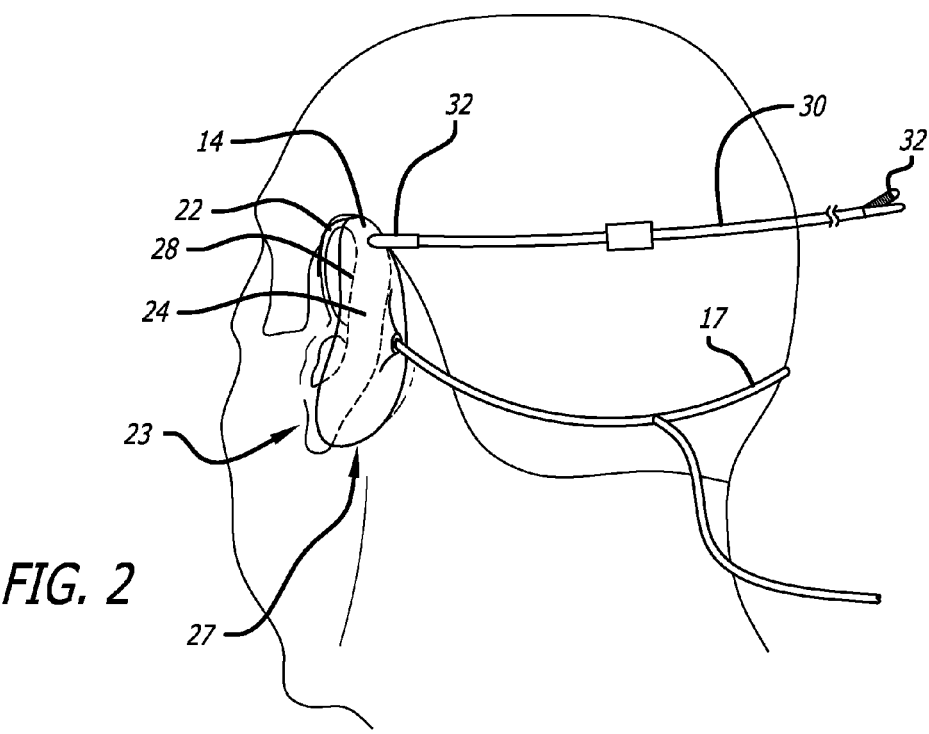
FIG. 2 is a perspective end view, depicting a mastoid ear cuff attached to an ear of a wearer and an adjustable headset.

In one aspect, the present invention is embodied in a system 10 for treating brain function (See FIGS. 1 and 2). The system includes one or more mastoid ear cuffs 12, 14 which are in electronic communication with a portable or hand-held signal generator 16. Leads 17 are provided to connect each ear cuff 12, 14 to the signal generator 16.

The ear cuff 12, 14 is cushioned for comfort and is designed to fit over and behind a person's ear. This design is particularly useful in the treatment of individuals who cannot endure objects placed over their ears such as a number of individuals afflicted with autism. The cuff 12, 14 is dimensioned to reach and engage the curve of the outer ear and to extend to a wearer's skull. In one particular embodiment, the cuff has a curved body 20 extending from the helix 22 of the ear 23 along Darwin's tubercle 24 and is configured with a ledge 26 designed to mate with the scaphoid fossa 28 of the ear. When placed on an ear, the body 20 further extends behind the ear 23 to the mastoid process area 29 of the skull.

Attached to the body 20 of the cuff 12, 14 is a wire 32 which is designed to fit along the helix 22 of the ear 23 or between the top of the ear 23 and the patient's head. The wire is intended to be plastic coated for comfort. Moreover, a lightweight, magnesium adjustable headset 30 having a pair of ends each equipped with a clamp 32 for engaging a body 20 of a ear cuff 12, 14 can additionally be provided to aid in securing the cuffs 12, 14 to a patient's head as well as ensuring a desired contact between the body 20 and a patient's mastoid process 30 area of his or her skull. In certain applications, it may be desirable to avoid having any portion of the cuff 12, 14 blocking the canal to the tympanic membrane of an ear. In this way, the cuff 12, 14 can be securely fitted to a patient without otherwise obstructing the hearing function.

As indicated, the present system contemplates two mastoid ear cuffs 12, 14 which are in communication with a signal generator. In one preferred embodiment, a single lead extends from each cuff 12, 14 and are joined together along in midsection 40 of the leads. The joined leads 17 extend therefrom to the signal generator 16. The leads 17 include a plug 42 which accomplishes a releasable or removable connection to the signal generator 16.

The signal generator 16 is capable of transmitting sound energy to the cuffs 12, 14 via leads 17. The signal generator 16 can include a display 46 which provides information concerning operation such as time, duration, mode or the like. A LED light 47 indicates usage or power. The device can also be equipped with a power switch 48 as well as a start/stop 49 and set/reset 50 buttons. A conventional adapter port 52 is also provided to thereby enable the system to be connected to an external power supply.

Figure 3:
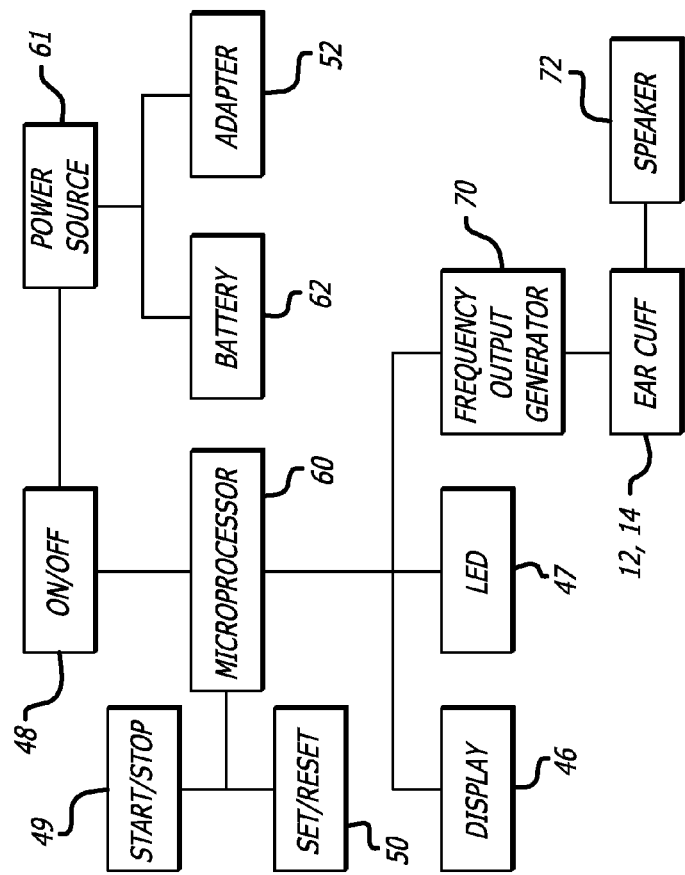
FIG. 3 is a schematic representation, depicting functions of the brain treatment system.

Turning now to FIG. 3, operation of the treatment system 10 is addressed. A key to the operation of the treatment system 10 is a microprocessor 60 that is programmed to control the generation of energy having desired frequencies. In one embodiment, power to the microprocessor 60 is controlled by the on/off switch 48. The power 61 itself can be provided by battery 62 or via the adapter port 52 which is connectable to a wall outlet or a conventional car power output such as a lighter bay (not shown).

Further external control of the function of the microprocessor 60 is found in the start/stop 49 and reset 50 buttons. As will be described in more detail below, treatment modalities include generating sound energies at various frequencies for pre-determined intervals. The start/stop button 49 initiates and ceases such treatment and the set/reset button 50 can be employed to begin a session, select a treatment modality or skip intervals should the same be desirable.

The programmed microprocessor 60 can be configured to communicate with the display 46, LED 47 and a frequency output 70. Information concerning a treatment modality is contemplated to be provided by the display 46 and the operation of the system 10 is reflected by an illuminated LED 47.

The energy generated by the frequency output generator 70 is also controlled by the microprocessor 60. After setting the treatment modality using the set/reset button 50 and thereafter pressing the start button 49, the microprocessor 60 sends signals corresponding to the selected treatment modality. The signal is received by the frequency output generator 70 which in turn sends signals to the ear cuffs 12, 14.

The mastoid ear cuff 12, 14 receives the signals from the generator 70 and the signals are received by speaker 72 contained within the ear cuff 12, 13. Such speakers 72 are contemplated to transmit both sound and vibrational energy in stereo. A volume or intensity control 74 can be configured into the ear cuff assembly 12, 14 or alternatively, such control can be integrated into the hand-held signal generator or auditory device 16 itself.

The treatment system 10 can be programmed to provide a myriad of frequencies of energy of varying character and for desired intervals or times. That is, frequencies close to one hertz to 44 hertz have been found to have benefits on a patient. Moreover, the pitch of sound energy is controllable by the treatment system.

Figure 4:
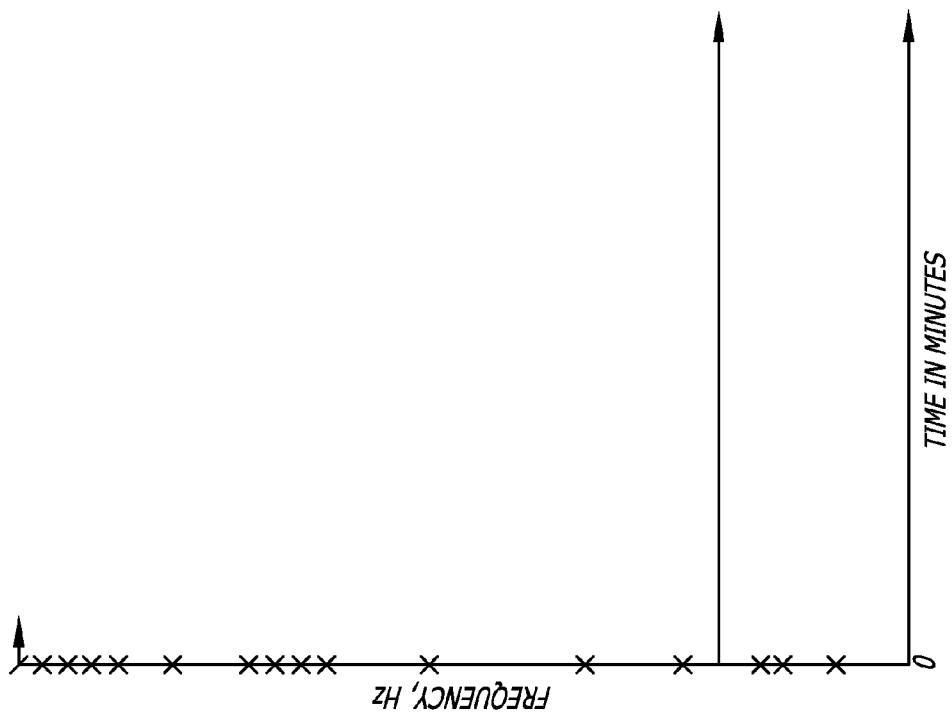
FIG. 4 is a graphical representation, depicting one frequency used in conjunction with teaching.

With reference to FIG. 4, there is shown one treatment modality to aid in learning. For individuals four years or older, auditory energy in a selected pitch and at 3 to 44 hertz is generated for a pre-determined duration in stereo through mastoid ear cuffs in order to synchronize the left and right hemispheres of the patient's brain. Other frequencies are also contemplated.

The purpose of the learning treatment modality is to assist a child or individual having auditory processing challenges, learning challenges and reading problems. The signal frequency application provides assistance with stimulating gentle synchronization of the hemispheres of the brain while taking into consideration auditory processing centers of the brain as well as sensory and motor regions of the brain. Thus, the approach enhances stabilization of emotional states, the ability to hear, speak and eventually read and to stimulate alertness. A square wave is employed to achieve desired results.

Figure 5:
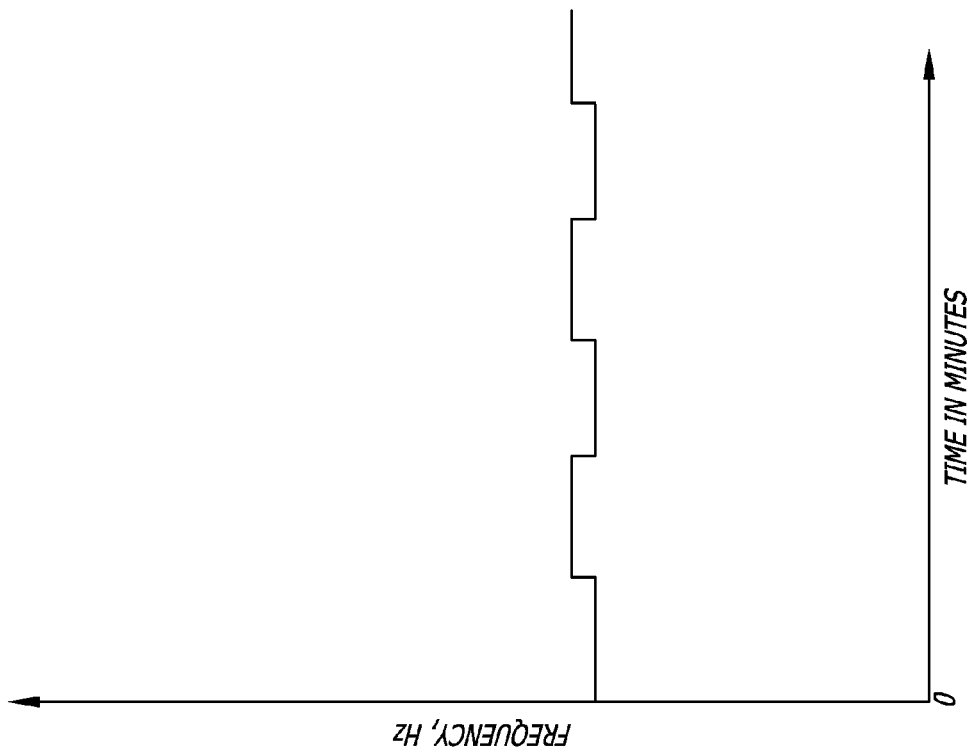
FIG. 5 is a graphical representation, depicting frequencies used to address sleepiness.

Turning now to FIG. 5, a treatment modality for staying awake is presented. This particular modality is useful for students of thirteen years of age or more who have trouble paying attention in class or who have trouble staying awake during long lectures and during studying. This approach is also helpful to students who tend to enter a trance while at a computer terminal. Either square or sign waves can be used in the generation of alternating energy for desired increments of time. The duration of the session can be set to achieve the desired results.

Through a multiple frequency approach, the treated subject is provided with various benefits. Alertness is stimulated as is the stabilization of emotional stress as is the clearing of emotional trauma or energy blocks. Clarity of thought and mental function are also enhanced.

Figure 6:
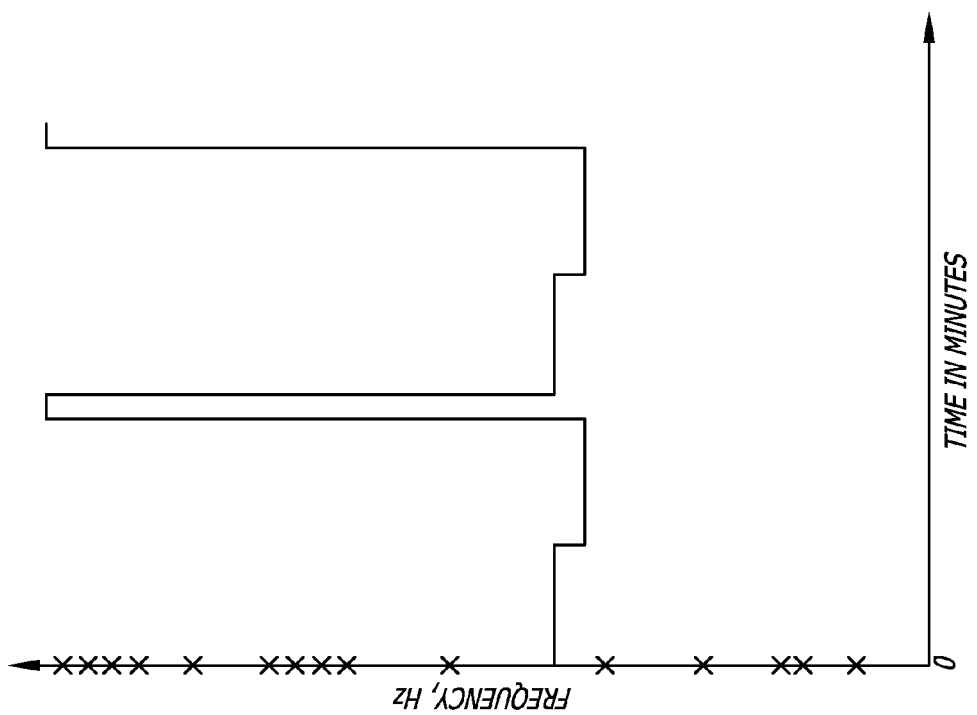
FIG. 6 is a graphical representation, depicting frequencies used to address stress and consciousness levels.

Another treatment modality is shown in FIG. 6. Here, the aim is to for example, assist a driver to stay awake and to simultaneously reduce the possibility of "road rage." As such, this modality is intended for those sixteen years of age or older. Again, a multiple frequency approach for a predetermined time can be repeated continuously in order to achieve desired results. Desired results include stimulating alertness, stimulating the stabilization of emotional states, stimulating the clearing of emotional trauma and energy blocks and stimulating clarity of thought and mental function.

Accordingly, the present invention provides approaches to accomplish the treatment of brain function. Various modalities are contemplated to address specific needs. The system can be configured to provide energy frequencies for each treatment modality or for a single treatment modality and ear cuffs are provided to transfer such energy into the auditory canal as well as directly through the mastoid process.

Thus, it will be apparent from the foregoing that, while particular forms of the invention have been illustrated and described, various modifications can be made without the parting from the spirit and scope of the invention.

We claim:

1. A system for treating brain function of a patient, comprising:
    a microprocessor, the microprocessor capable of generating selected frequencies of energy; and
    at least one mastoid ear cuff, the mastoid ear cuff in communication with the microprocessor and including an ear engaging portion, a mastoid process portion, and an energy transmitter;
    wherein the selected frequency of energy is transmitted at least through a mastoid process of a patient;
    wherein the system lacks structure configured within a body of the patient.

2. The system of claim 1, wherein the energy is sound.

3. The system of claim 1, wherein the microprocessor is contained in a portable device and further comprising a lead connecting the mastoid ear cuff with the portable device.

4. The system of claim 1, wherein there are two mastoid ear cuffs in communication with the microprocessor.

5. The system of claim 4, further comprising a headband removably attachable to each of the ear cuffs.

6. The system of claim 4, further comprising a lead extending from each of the mastoid ear cuffs.

7. The system of claim 1, wherein the mastoid process portion is configured to engage a patient's skull in an area of a mastoid process.

8. The system of claim 1, wherein the mastoid ear cuff lacks a structure covering an opening leading to a patient's tympanic membrane.

9. The system of claim 1, wherein the mastoid ear cuff transmits sound and vibration to a patient.

10. The system of claim 1, wherein the mastoid ear cuff further comprises a wire extending from a foam-like portion.

11. The system of claim 10, wherein the foam-like portion is configured to mate with a Darwin's tubercle of a patient's ear.

12. The system of claim 10, wherein the wire is configured to extend along a helix of a patient's ear.

13. The system of claim 1, wherein the microprocessor generates energy at frequencies selected to treat sleepiness.

14. The system of claim 1, wherein the microprocessor generates energy at frequencies selected to enhance learning.

15. The system of claim 1, wherein the microprocessor generates energy at frequencies selected to enhance concentration.

16. The system of claim 1, further comprising a portable device having a power supply in communication with the microprocessor.

17. The system of claim 16, wherein the portable device further comprises an LED indicating use.

18. The system of claim 16, further comprising an adapter that connects the portable device to the mastoid ear cuffs.

19. The system of claim 1, further comprising means for synchronizing left and right hemispheres of a patient's brain.

20. The system of claim 1, wherein the system lacks structure for enhancing or testing a hearing function of the patient.

* * * * *